United States Patent [19]

Zubler

[11] Patent Number: 5,033,238
[45] Date of Patent: Jul. 23, 1991

[54] DENTAL TECHNICIAN'S WORK STATION

[76] Inventor: Kurt Zubler, Ginsterweg 28, D-7910 Neu-Ulm, Fed. Rep. of Germany

[21] Appl. No.: 353,561

[22] Filed: May 18, 1989

[30] Foreign Application Priority Data

May 20, 1988 [DE] Fed. Rep. of Germany ....... 3817347
May 20, 1988 [DE] Fed. Rep. of Germany ....... 3817364

[51] Int. Cl.$^5$ .............................................. B24B 55/06
[52] U.S. Cl. .............................. 51/165.74; 51/165.71; 51/273; 51/5 B
[58] Field of Search ............. 51/3, 273, 165.74, 134.5, 51/165.71, 5 B, 5 C

[56] References Cited

U.S. PATENT DOCUMENTS

| 2,419,744 | 4/1947 | Thwaites | 51/273 |
| 4,227,902 | 10/1980 | Olson | 51/273 |
| 4,887,221 | 12/1989 | Davis et al. | 51/165.71 |

FOREIGN PATENT DOCUMENTS

| 2846146 | 5/1979 | Fed. Rep. of Germany | 51/3 |
| DE3328875 | 8/1983 | Fed. Rep. of Germany | |
| 0185573 | 8/1988 | Japan | 51/165.74 |

Primary Examiner—Robert A. Rose
Attorney, Agent, or Firm—Lowe, Price, LeBlanc and Becker

[57] ABSTRACT

A dental technician's work station is provided with a hand-held machining device and a suction device for removal of dust resulting from machining. Connection of the machining device to the suction device by a common data bus is provided, and the parameters corresponding to the machining device are input and used to control both the hand-held machining device and the suction device. The suction device is thus always adjusted automatically to match the respective handling step using a specific machining bit. An especially fast and certain adjustment of the machining unit and/or the suction device by means of selector keys is effected, these keys having respective symbols for the particular machining bits utilized. The speed of the matching unit and, in an especially advantageous embodiment, the suction device as well, are thus adjusted correctly and simultaneously with a single key stroke.

5 Claims, 2 Drawing Sheets

DENTAL TECHNICIAN'S WORK STATION

FIELD OF THE INVENTION

The invention relates to a dental technician's work station on which models of teeth and dentures (protheses) are prepared in several procedural steps.

BACKGROUND OF THE INVENTION

German Patent No. 33 28 875 discloses a dental technician's work station using a suction device which serves to remove dust caused by grinding or milling plastic, plaster or metal models with a hand grinder. The type of machining bit used in the typical rotary machine device held by the technician varies according to the material to be treated and the degree of precision of the particular working step, for example, coarse milling or fine grinding; and various machining bit types require different speeds. Experience has shown that the speed of the grinder and/or the suction device is very often incorrectly set by the user; calculating or estimating errors are usually responsible for inaccurate speed settings. A speed adjustment when the machining bit or work piece is changed is often not performed, not only on the hand grinder but also on the suction device, since speed adjustment on the known grinding or suction tools is often complicated and time consuming.

In dental technology, a wide range of machining bits is used, from disk millers or cutting disks with up to 50 mm diameter at one end of the scale to polishing heads with just a few millimeters diameter at the other end. Dependent on the cutting material used, for example hardened alloys or diamond, machining bit manufacturers recommend varying cutting speeds. If the speed is unduly high as a result of a faulty or omitted speed setting, there is the danger that machining bit portions such as cutting disks or diamond particles are split off due to the increased peripheral speed, thus endangering the dental technician. On the other hand, if the peripheral speed set is too low, the surface finish and cutting performance of the grinder are adversely affected.

The suction device is also adversely affected if the speed of the suction fan is too high or low. If too high, than excessive noise occurs at the work station, as well as high energy consumption; a low speed not matching the particular work stage results in insufficient suction by the suction fan, hence the dust from grinding is inhaled by the dental technician or may settle in the surroundings.

SUMMARY OF THE DISCLOSURE

Accordingly, it is a principal object of this invention to provide a dental technician's work station equipped with improved setting means for machining and suction devices used thereat.

It is a further object of the invention to provide a dental technician's work station having a simplified and easy-to-use speed adjustment on the machining device and suction device.

It is a still further object of the invention to provide a dental technician's work station having an especially fast and positive speed adjustment by an improved operating device.

Accordingly, a work station for dental technological purposes according to a preferred embodiment of the invention comprises a machining means having an adjustable rotational speed and adapted for using one of a plurality of different machining bits; a suction means for removal of dust resulting from machining of a model of teeth or dentures by means of said machining device; an operating unit including input means for entering machining bit-identifying data; and control means for setting said rotational speed of said machining device and a throughput of said suction means dependent on said identifying data.

This configuration not only switches on the suction device automatically when the machining device is switched on, but also brings about automatic adjustment upon operating changes, so that the suction device is most effectively matched to the speed of the grinder, to the actual working step, and/or to the material to be machined. A seperate speed adjustment on the suction unit is thus not needed. Operation is considerably simplified by the units linked to each other. Energy consumption and noise are limited to a minimum level. Instead of the usual multiple speed adjustments both on the grinder and the suction unit, speed adjustment, according to the invention, needs to be made on the grinder only; the speed of the suction unit is automatically adjusted via the common data line to the suction unit and is matched to the particular speed set on the hand grinder. In addition, faulty adjustment of the suction unit in relation to the speed of the grinder cannot occur due to speed data defined and stored by the manufacturer.

In a preferred embodiment, selector keys for the material to be machined are provided on the operating unit for speed adjustment of the grinder; a possible inscription might be "plaster - coarse milling". The grinder speed is thus set in relation to a particular speed stored for this purpose; at the same time the command is passed to the suction device for a correspondingly suitable suction fan speed stored in another memory section. Since more dust will be expected from machining a plaster (e.g., Plaster of Paris) than, for example, a metal, the suction unit speed is automatically set higher for a plaster than for the key "metal milling".

It is also advantageous that the data line linking the machining and suction devices allow the display on the operating unit of service instructions from the suction unit. Since the operating unit is always within the view of the dental technician, service instructions from the suction device such as "change filter", cannot be overlooked, as is often the case on equipment in the under-the-table arrangement of the suction unit. In addition, the invention provides for a linking of the machining and suction devices; electrical components such as power packs or frequency converters are common to both units, preferably arranged on a common base. A markedly simplified manufacture results, whereas until now the machining and suction units were manufactured and sold completely separate from each other.

According to another aspect of the invention, a dental technician's work station is provided, including an operating device for the hand-held machining device, formed as a keyboard for speed adjustment, the keys having symbols for the various machining machining bits and each key being assigned a stored speed value corresponding to the symbol of a machining machining bit.

According to this embodiment of the invention, the operating unit makes calculations unnecessary for the dental technician and errors in speed adjustment are avoided with certainty. This results in a considerable increase in work safety and economy of operation since the respective machining machining bit is always operated with the most effective speed recommended by the manufacturer. Unduly high speeds resulting in a danger to safety are thus impossible.

In addition, this operating unit allows extremely fast speed adjustment since a single key entry is sufficient to choose the speed to match a particular machining application and to operate the machining device. Each machining bit is thus identified by the key entry such that in addition to the matching speed value set on the machining device, the overall operating period or the maximum permissible torque of the chosen machining bit is shown and/or set automatically. At the same time, it is possible for an operator of the device, using specific data stored for the chosen machining bit, to adjust the speed of the suction device, so that, for example, the suction volume corresponding to especially dusty plaster of paris treatment is set by a suitable speed increase on the suction device.

The operating unit is especially suitable for inexperienced dental technicians since the visual determination of the inserted machining bit is very easy; the invention is favored by the fact that in dental laboratories only relatively few machining bits are used for the most frequent working steps and these differ widely in size and shape, so that adequate differentiation between individual machining bits is possible at a glance.

Further features and advantages of the invention will become apparent from the following description of embodiments with reference to the drawings.

DESCRIPTION OF A PREFERRED EMBODIMENT

Figure 1:
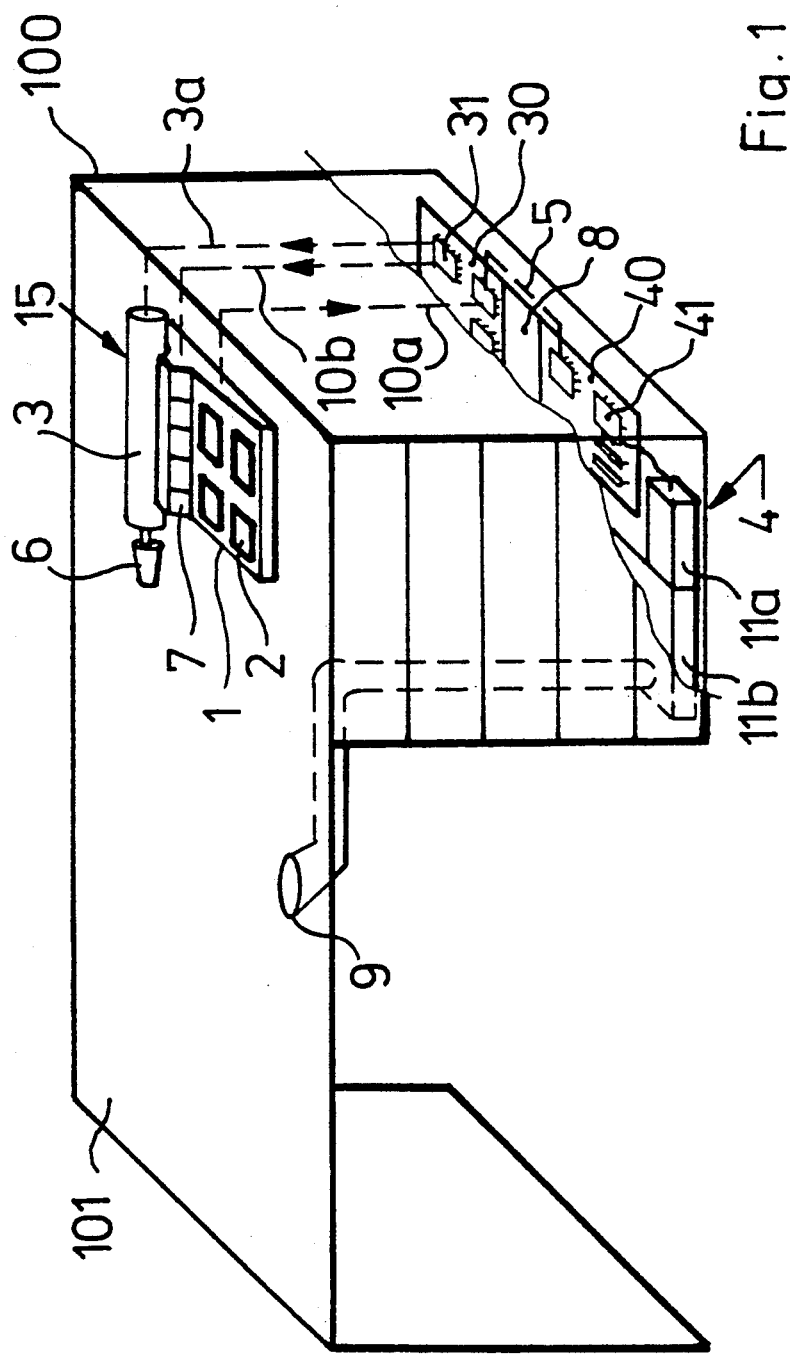
FIG. 1 shows a perspective elevational view of a dental technician's work station.
Figure 2:
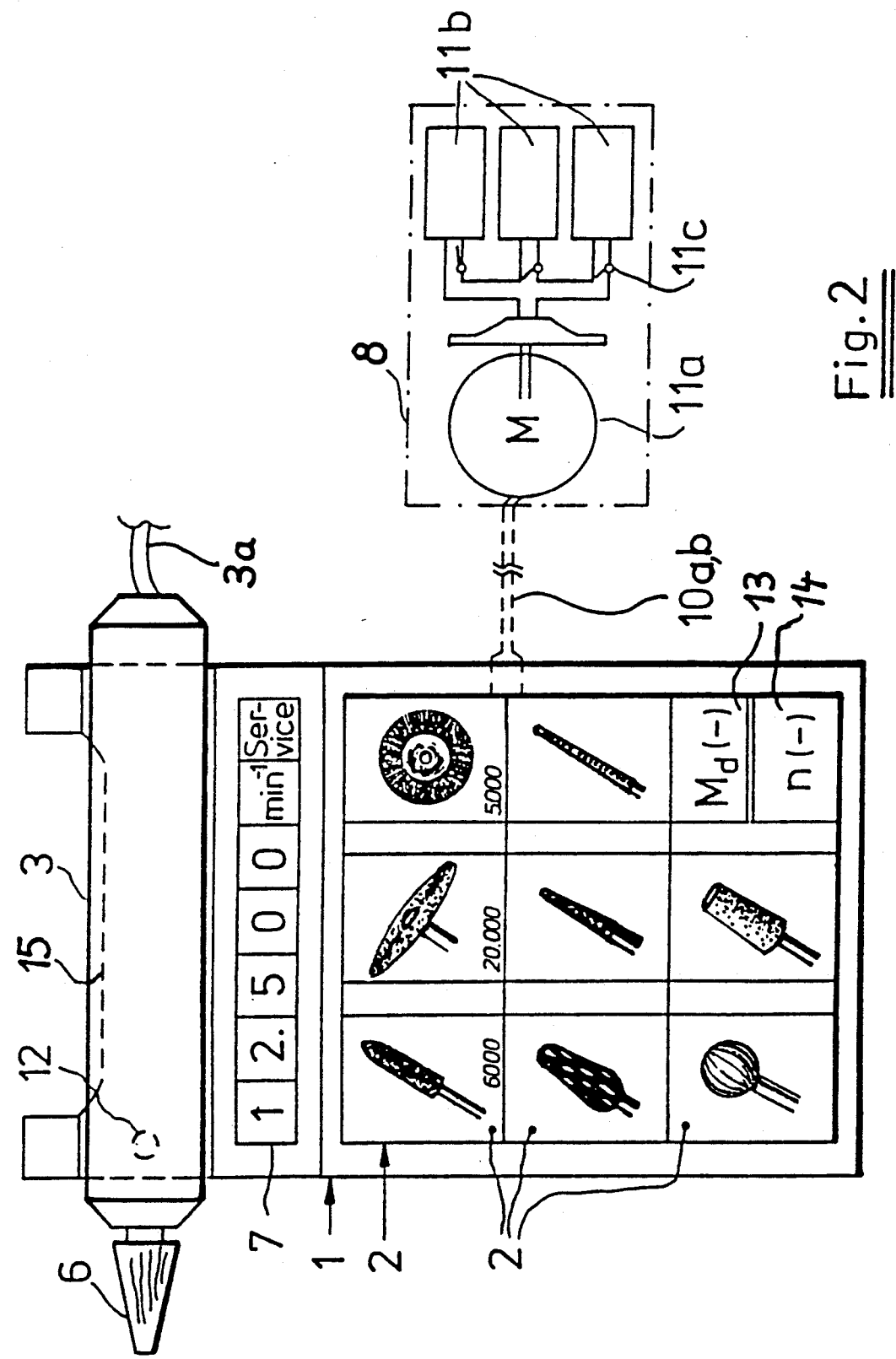
FIG. 2 shows an enlarged illustration of the operating device on the dental technician's station.

FIG. 1 is a diagram of a dental technician's work station 100 on a top platform 101 of which an operating unit 1 is arranged including a keyboard having several selector keys 2. For example, four selector keys 2 may be provided with the inscriptions "PLASTER OF PARIS: COARSE MACHINING; " "PLASTER OF PARIS: FINE MACHINING;" "METAL:COARSE MACHINING;" "METAL: FINE MACHINING." According to the number of working steps to be performed, correspondingly more keys may be provided, as shown in FIG. 2. In a support 15 of the operating unit 1 a machining device 3, e.g., in the form of a hand grinder is provided into which a variety of machining bits 6 may be inserted. The machining device 3 is connected to an associated control circuit 30 housed in a base of the dental technician's work station.

A suction device 4 including a suction motor 11a and filters 11b (see FIG. 2) is housed there as well as an electrical control circuit 40 associated to the suction device 4 and the suction motor 11a. According to the invention the two control circuits 30 and 40 are connected via a data line or bus 5, and are arranged on a common plate 8 adjacent to the suction motor 11a, such that the entire base 8 may be cooled by the suction air stream. In this way plate 8 comprises the electronical elements of the control circuits 30, 40. The suction device 4 is connected via a suction channel 9 to a dust suction funnel on the top of the work table. The suction device 4 may be located at the bottom side of the work table to save space, since the operation of the suction unit 4 is performed exclusively by the operating unit 1. This type of remote control allows placing of the suction device 4 anywhere; the suction device 4 may be arranged as shown in FIG. 1 close to the left-hand table leg or next to the work station.

In addition to a power line 3a from the control circuit 30 to the machining device 3, two transmission cables 10a, 10b lead from the common plate 8 or the control circuit 30 to the operating unit 1 and a display 7 thereof. The transmission cable 10a transmits the speed values entered by the selector keys 2 first to the control circuit 30 and further via the data line 5 to the control circuit 40, as indicated by the arrow pointing downward. The second transmission cable 10b passes information from the control circuit 40 (via the data line 5) and from the control circuit 30 to the display device 7. In this way, service instructions for the suction device 4 may be displayed with the set speed of the machining device 3 or the currently set air flow value of the suction device 4, as FIG. 2 shows in more detail. It should be noted that cables 10a, 10b may be connected to control circuit 40 and also to the control circuit 30 of the machining device 3 by data line 5.

FIG. 2 shows the operating unit 1 in an enlarged manner; the reference numbers are identical to those used in FIG. 1. In FIG. 2 the special configuration of the selector keys 2 is shown in the form of symbols. The surfaces of the selector keys 2 illustrate a various machining tools commonly used in dental technology: the lower middle key corresponds, for example, to the machining bit inserted in the hand-held machining device 3. The symbols on the selector keys 2 are preferably pictographic representations of the machining bit 6 which can supplemented by diameter data. After insertion of the machining bit 6 into the machining device 3, the dental technician presses the corresponding key 2, a programmed speed value in a memory module 31 (e.g. an EEPROM) of the control circuit 30 being fetched via the transmission cable 10a. The suction device 4 may then be controlled corresponding to the chosen machining tool 6 according to the material to be machined and resulting dust amount via the data line 5 shown in FIG. 1. For this purpose, an electronic memory module 41 is provided in the control circuit 40, the module 41 storing values for the parameters ( e.g. throughput) of the suction motor 11a. A speed value is fetched via the data line 5 after signaling of the set speed of the machining 6.

A contact switch 12 is provided at the operating unit 1, for switching on the machining device 3 automatically when it is removed from the support 15 of the technician-held machining device 3. The machining device 3 rotates with the speed selected by pressing one of the keys 2. Removal of the machining device 3 switches on, as explained above, the suction device 4 at the same time, operating at the speed chosen by the selector keys 2 via the data line 5 from memory 41. A single key stroke thus sets not only the correct speed of the machining device 3 but also simultaneously sets the appropriate speed of the suction motor 11a of the suction device 4. By clear identification of the inserted tool 6 the corresponding speed is thus obtained from the memory 31 by means of a single key stroke matching the machining 6 and automatically at the machining device 3. This determination of the inserted machining 6 by means of a single stroke of a selector key 2 allows an adjustment of the suction amount (throughput) corresponding to the dust amount resulting from the respective machining work by speed increase or reduction. In this way, a single key stroke on the keyboard may switch the system over to one of various filters 11b, since for plaster of paris work other filters are used than for milling gold or plastic.

Since each of the selector keys 2 represents a completely different machining bit 6, the choice of the respective machining bit 6 may lead to the activation of the corresponding filter by control of the schematically indicated flaps 11c (FIG. 2) in the suction channel to the individual filters 11b. The required programs for this purpose are also stored in the memory element 41. The keys 2 in the top row of the operating unit 1 may be provided, for example, for machining bits for machining plaster of paris, and the topmost filter 11b, here set for passage of air flow, may be a corresponding coarse filter for plaster of paris dust. The middle row of keys provided with machining bit symbols could be, for example, machining bits for the plastic machining of dentures, so that the operation switches over to the medium filter 11b. Similarly, the bottom row of the selector keys 2 symbolizing machining bits 6 for metal machining, may be chosen to select a correspondingly fine filter 11b via the control of the flaps 11c, e.g., by magnetic actuators or valves (not shown).

Additional keys 13 and 14 may be provided in the operating unit 1 to reduce torque and/or speed relative to the stored values. This is especially called for when dentures are fine-machined, an especially low torque of the machining bit 6 being required to prevent groove marks. Obviously, further keys corresponding to these additional keys 13 and 14 may be arranged to increase torque if, for example, increased torque is required for cutting by grinding on metal dentures. With the invention, use is made of the fact that certain machining bits 6 can be used only for fine work and other machining bits 6 only for coarse work with correspondingly high speed or torque. Due to the clear visual identification of the inserted machining bit 6, the corresponding speed and torque required for this machining stage are read from memory module 31 of the control circuit 30 by means of a single key stroke matching the machining bit 6 and set automatically at the machining device 3. Especially advantageous is the connection and coupling to the suction device 4 by means of the data line 5 and the matching speed setting via the control circuit 40 and its memory module 41. In both memories 31 and 41, which also can be integrated into a single electronic module such as an EEPROM, limiting values may be programmed in addition for the maximum load permitted of the machining device 3 and the suction device 4. If the permitted torque of the respective machining bit 6 or the capacity of the filter 11b are exceeded, warning instructions are displayed on the display 7 to require servicing.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

I claim:

1. A work station for dental technological purposes, comprising:
    a hand-held machining device having an adjustable rotational speed and adapted for utilizing one of a plurality of different machining bits;
    a suction means for removal of dust resulting from machining of a model of teeth or denture by means of said hand-held machining device;
    an operating unit including a plurality of keys individually provided with symbols designating one of said machining bits for entering machining bit identifying data by a single key entry; and
    control means for setting said rotational speed of said hand-held machining device and a corresponding suction draft of said suction means dependent on said identifying data via a common data-bus means.

2. The work station of claim 1, wherein:
    said operating unit further comprises a support means for said hand-held machining device, said support means being provided with an activating switch for switching on said hand-held machining device upon removal from said support and for switching off said hand-held machining device upon placement thereof onto said support.

3. The work station of claim 1, wherein:
    said control means includes memory means for storing operational parameters of said hand-held machining device, and said operating unit further comprises a display means for displaying said parameters.

4. The work station of claim 1, wherein:
    said suction means further comprises a plurality of filter means selectively activated for passage of suction flow therethrough dependent on a signal of said control means.

5. A work station for dental technological purposes, comprising:
    a hand-held machining device having an adjustable rotational speed and adapted for utilizing a selected one of a plurality of different machining bits;
    a suction means for removal of dust resulting from machining of a model of teeth or denture by means of said machining device;
    an operating unit including input means for entering machining-bit identifying data and control means comprising a plurality of keys each of which is associated with one of said machining bits and memory means for storing data relating to said rotational speed of said machining device and to said suction draft of said suction means, for setting said rotational speed of said machining device and a throughput of said suction means dependent on said identifying data upon selection by a predetermined key; and
    a support means for said machining device incorporated in said operating device, said support means being provided with an activating switch for switching on said machining device upon removal from said support and for switching off said machining device upon placement thereof onto said support.

* * * * *